(12) United States Patent
Kwok et al.

(10) Patent No.: US 8,894,568 B2
(45) Date of Patent: Nov. 25, 2014

(54) NORMALIZATION AND STABILIZATION OF BALLOON SURFACES FOR DEFLATION

(75) Inventors: Jason Kwok, Anaheim, CA (US); Robert Pecor, Aliso Viejo, CA (US); Mark Ashby, Laguna Niguel, CA (US); Selene Chida, Irvine, CA (US); Outhit Bouasaysy, Corona, CA (US)

(73) Assignee: ReShape Medical, Inc., San Clemente, CA (US)

(*) Notice: Subject to any disclaimer, the term of this patent is extended or adjusted under 35 U.S.C. 154(b) by 0 days.

(21) Appl. No.: 13/389,221

(22) PCT Filed: Sep. 24, 2010

(86) PCT No.: PCT/US2010/050260
§ 371 (c)(1),
(2), (4) Date: Sep. 21, 2012

(87) PCT Pub. No.: WO2011/038270
PCT Pub. Date: Mar. 31, 2011

(65) Prior Publication Data
US 2013/0066267 A1    Mar. 14, 2013

Related U.S. Application Data

(60) Provisional application No. 61/245,630, filed on Sep. 24, 2009, provisional application No. 61/330,188, filed on Apr. 30, 2010.

(51) Int. Cl.
| | | |
|---|---|---|
| A61B 1/00 | (2006.01) | |
| A61B 17/34 | (2006.01) | |
| A61F 5/00 | (2006.01) | |
| A61B 17/22 | (2006.01) | |
| A61M 25/09 | (2006.01) | |
| A61M 25/10 | (2013.01) | |
| A61M 25/00 | (2006.01) | |

(52) U.S. Cl.
CPC ..... *A61F 5/0089* (2013.01); *A61B 2017/22035* (2013.01); *A61M 2025/09183* (2013.01); *A61M 25/1018* (2013.01); *A61M 2025/0095* (2013.01); *A61B 1/0008* (2013.01)

USPC .......... 600/129; 606/185; 606/192; 606/106; 604/99.01

(58) Field of Classification Search
CPC ... A61F 5/0036; A61F 5/0043; A61F 5/0076; A61F 5/0089; A61F 5/0056; A61B 1/0008; A61B 1/018; A61B 1/015; A61B 1/00071; A61B 2017/306
USPC ............... 604/99.01; 600/101, 128, 129, 130, 600/139–152; 606/185, 192
See application file for complete search history.

(56) References Cited

U.S. PATENT DOCUMENTS

| | | |
|---|---|---|
| 2,493,326 A | 1/1950 | Trinder |
| 4,133,315 A | 1/1979 | Berman et al. |

(Continued)

FOREIGN PATENT DOCUMENTS

| | | |
|---|---|---|
| DE | 8708978 U1 | 11/1987 |
| EP | 0103481 | 3/1984 |

(Continued)

OTHER PUBLICATIONS

Non-Final Office Action; U.S. Appl. No. 11/263,302; dated: Oct. 9, 2012, 6 pages.

(Continued)

*Primary Examiner* — Nicholas Lucchesi
*Assistant Examiner* — Leah Stohr
(74) *Attorney, Agent, or Firm* — Perkins Coie LLP

(57) ABSTRACT

A deflation device for use in deflating an inflatable or implantable balloon device, comprising, in combination: an endoscope tube, having a distal end, a proximal end, and a lumen; a cap disposed at the distal end of the endoscope tube and having walls defining a balloon interface chamber; a coring device disposed within the lumen and configured to travel within the lumen such that a distal end of the coring device is extendable beyond the distal end of the cap; wherein the cap is configured to provide a normal surface of a balloon relative to the orientation of the coring device as the coring device is disposed near the distal end of the cap.

21 Claims, 10 Drawing Sheets

(56) References Cited

U.S. PATENT DOCUMENTS

| | | | |
|---|---|---|---|
| 4,198,983 A | 4/1980 | Becker et al. | |
| 4,246,893 A | 1/1981 | Berson | |
| 4,356,824 A | 11/1982 | Vazquez | |
| 4,416,267 A | 11/1983 | Garren et al. | |
| 4,465,072 A | 8/1984 | Taheri | |
| 4,465,818 A | 8/1984 | Shirahata et al. | |
| 4,485,805 A | 12/1984 | Foster, Jr. et al. | |
| 4,543,089 A | 9/1985 | Moss | |
| 4,598,699 A | 7/1986 | Garren et al. | |
| 4,694,827 A | 9/1987 | Weiner et al. | |
| 4,723,547 A | 2/1988 | Kullas et al. | |
| 4,899,747 A | 2/1990 | Garren et al. | |
| 4,940,458 A | 7/1990 | Cohn | |
| 5,073,347 A | 12/1991 | Garren et al. | |
| 5,084,061 A | 1/1992 | Gau et al. | |
| 5,123,840 A | 6/1992 | Nates | |
| 5,234,454 A | 8/1993 | Bangs | |
| 5,259,399 A | 11/1993 | Brown | |
| 5,263,934 A | 11/1993 | van den Haak | |
| 5,273,536 A | 12/1993 | Savas | |
| 5,318,530 A | 6/1994 | Nelson | |
| 5,334,187 A | 8/1994 | Fischell et al. | |
| 5,431,173 A | 7/1995 | Chin et al. | |
| 5,496,271 A | 3/1996 | Burton et al. | |
| 5,575,772 A | 11/1996 | Lennox | |
| 5,643,209 A | 7/1997 | Fugoso et al. | |
| 5,730,722 A | 3/1998 | Wilk | |
| 5,779,728 A | 7/1998 | Lunsford et al. | |
| 5,857,991 A | 1/1999 | Grothoff et al. | |
| 5,876,376 A | 3/1999 | Schwab et al. | |
| 5,938,669 A | 8/1999 | Klaiber et al. | |
| 5,993,473 A | 11/1999 | Chan | |
| 5,997,503 A | 12/1999 | Willis et al. | |
| 6,149,621 A | 11/2000 | Makihara | |
| 6,254,355 B1 | 7/2001 | Gharib | |
| 6,276,567 B1 | 8/2001 | Diaz et al. | |
| 6,280,411 B1 | 8/2001 | Lennox | |
| 6,423,058 B1 | 7/2002 | Edwards et al. | |
| 6,427,089 B1 | 7/2002 | Knowlton | |
| 6,454,785 B2 | 9/2002 | De Hoyos Garza | |
| 6,524,234 B2 * | 2/2003 | Ouchi | 600/127 |
| 6,535,764 B2 | 3/2003 | Imran et al. | |
| 6,547,788 B1 | 4/2003 | Maguire et al. | |
| 6,579,301 B1 | 6/2003 | Bales et al. | |
| 6,592,552 B1 | 7/2003 | Schmidt | |
| 6,613,018 B2 | 9/2003 | Bagga et al. | |
| 6,613,037 B2 | 9/2003 | Khosravi et al. | |
| 6,706,010 B1 | 3/2004 | Miki et al. | |
| 6,746,460 B2 | 6/2004 | Gannoe et al. | |
| 6,826,428 B1 | 11/2004 | Chen et al. | |
| 6,850,128 B2 | 2/2005 | Park | |
| 6,866,657 B2 | 3/2005 | Shchervinsky et al. | |
| 6,869,431 B2 | 3/2005 | Maguire et al. | |
| 6,890,300 B2 | 5/2005 | Lloyd et al. | |
| 6,890,346 B2 | 5/2005 | Ganz et al. | |
| 6,902,535 B2 | 6/2005 | Eberhart et al. | |
| 6,923,754 B2 | 8/2005 | Lubock | |
| 6,931,286 B2 | 8/2005 | Sigg et al. | |
| 6,939,299 B1 | 9/2005 | Petersen et al. | |
| 6,958,052 B1 | 10/2005 | Charlton | |
| 7,001,419 B2 | 2/2006 | DiCapino et al. | |
| 7,016,735 B2 | 3/2006 | Imran et al. | |
| 7,020,531 B1 | 3/2006 | Colliou et al. | |
| 7,033,373 B2 | 4/2006 | De la Torre et al. | |
| 7,056,305 B2 | 6/2006 | Garza Alvarez | |
| 7,076,305 B2 | 7/2006 | Imran et al. | |
| 7,081,125 B2 | 7/2006 | Edwards et al. | |
| 7,131,945 B2 | 11/2006 | Fink et al. | |
| 7,483,746 B2 | 1/2009 | Lee et al. | |
| 7,625,355 B2 | 12/2009 | Yu | |
| 7,828,749 B2 | 11/2010 | Douglas et al. | |
| 8,083,757 B2 | 12/2011 | Gannoe et al. | |
| 2001/0022988 A1 | 9/2001 | Schwarz et al. | |
| 2001/0037127 A1 | 11/2001 | De Hoyos Garza | |
| 2002/0055757 A1 | 5/2002 | Torre | |
| 2002/0107515 A1 | 8/2002 | Edwards et al. | |
| 2002/0161388 A1 | 10/2002 | Samuels et al. | |
| 2002/0173804 A1 | 11/2002 | Rousseau | |
| 2003/0114878 A1 | 6/2003 | Diederich et al. | |
| 2003/0171768 A1 | 9/2003 | McGhan | |
| 2003/0187390 A1 | 10/2003 | Bates et al. | |
| 2004/0044354 A1 | 3/2004 | Gannoe et al. | |
| 2004/0059289 A1 | 3/2004 | Garva Alvarez | |
| 2004/0059290 A1 | 3/2004 | Palasis | |
| 2004/0073162 A1 | 4/2004 | Bleam et al. | |
| 2004/0087902 A1 | 5/2004 | Richter | |
| 2004/0106899 A1 | 6/2004 | McMichael et al. | |
| 2004/0116897 A1 | 6/2004 | Aboul-Hosn | |
| 2004/0127915 A1 | 7/2004 | Fleenor et al. | |
| 2004/0186502 A1 | 9/2004 | Sampson et al. | |
| 2004/0220665 A1 | 11/2004 | Hossainy | |
| 2004/0236280 A1 | 11/2004 | Rice et al. | |
| 2004/0236361 A1 | 11/2004 | Sakurai | |
| 2004/0254600 A1 | 12/2004 | Zarbatany et al. | |
| 2005/0027283 A1 | 2/2005 | Richard et al. | |
| 2005/0027313 A1 | 2/2005 | Shaker | |
| 2005/0038415 A1 | 2/2005 | Rohr et al. | |
| 2005/0055039 A1 | 3/2005 | Burnett et al. | |
| 2005/0059990 A1 | 3/2005 | Ayala | |
| 2005/0075624 A1 | 4/2005 | Miesel | |
| 2005/0085792 A1 | 4/2005 | Gershowitz | |
| 2005/0119674 A1 | 6/2005 | Gingras et al. | |
| 2005/0131442 A1 | 6/2005 | Yachia et al. | |
| 2005/0143784 A1 | 6/2005 | Imran | |
| 2005/0159769 A1 | 7/2005 | Alverdy | |
| 2005/0177103 A1 | 8/2005 | Hunter et al. | |
| 2005/0192615 A1 | 9/2005 | Torre et al. | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2006/0058829 A1 | 3/2006 | Sampson et al. | |
| 2006/0178691 A1 | 8/2006 | Binmoeller | |
| 2006/0184112 A1 | 8/2006 | Horn et al. | |
| 2006/0259020 A1 | 11/2006 | Sharratt | |
| 2007/0016262 A1 | 1/2007 | Gross et al. | |
| 2007/0093728 A1 | 4/2007 | Douglas et al. | |
| 2007/0100367 A1 | 5/2007 | Quijano | |
| 2007/0100368 A1 | 5/2007 | Quijano | |
| 2007/0100369 A1 | 5/2007 | Cragg | |
| 2007/0142770 A1 | 6/2007 | Rioux et al. | |
| 2007/0149994 A1 | 6/2007 | Sosnowski | |
| 2007/0173881 A1 | 7/2007 | Birk et al. | |
| 2007/0233161 A1 | 10/2007 | Weller et al. | |
| 2007/0250020 A1 | 10/2007 | Kim et al. | |
| 2007/0265369 A1 | 11/2007 | Muratoglu et al. | |
| 2007/0265598 A1 | 11/2007 | Karasik | |
| 2007/0288033 A1 | 12/2007 | Murature et al. | |
| 2008/0058887 A1 | 3/2008 | Griffin et al. | |
| 2008/0082056 A1 | 4/2008 | Mauch et al. | |
| 2008/0097513 A1 | 4/2008 | Kaji et al. | |
| 2008/0119729 A1 | 5/2008 | Copa et al. | |
| 2008/0172079 A1 | 7/2008 | Birk | |
| 2008/0190363 A1 | 8/2008 | Chen et al. | |
| 2008/0208241 A1 | 8/2008 | Weiner et al. | |
| 2008/0233167 A1 | 9/2008 | Li et al. | |
| 2008/0243071 A1 | 10/2008 | Quijano | |
| 2008/0243166 A1 | 10/2008 | Paganon et al. | |
| 2008/0255601 A1 | 10/2008 | Birk | |
| 2008/0319471 A1 | 12/2008 | Sosnowski et al. | |
| 2009/0048624 A1 | 2/2009 | Alverdy | |
| 2009/0275973 A1 | 11/2009 | Chen et al. | |
| 2010/0023047 A1 | 1/2010 | Simpson | |
| 2010/0130998 A1 | 5/2010 | Alverdy | |
| 2010/0243135 A1 | 9/2010 | Pepper et al. | |
| 2010/0251837 A1 | 10/2010 | Bouasaysy et al. | |
| 2011/0178544 A1 | 7/2011 | Sosnowski et al. | |
| 2012/0271336 A1 | 10/2012 | Hamman et al. | |
| 2012/0289992 A1 | 11/2012 | Quijano et al. | |

FOREIGN PATENT DOCUMENTS

| | | |
|---|---|---|
| EP | 0457456 | 5/1990 |
| EP | 0485903 | 8/1991 |
| EP | 1781183 | 5/2007 |

(56) References Cited

FOREIGN PATENT DOCUMENTS

| | | |
|---|---|---|
| FR | 2862525 | 5/2005 |
| GB | 2139902 | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| WO | WO-0141700 | 6/2001 |
| WO | WO-0166166 A2 | 9/2001 |
| WO | WO2006035446 | 4/2006 |
| WO | WO-2006056944 A1 | 6/2006 |
| WO | WO2006/128978 | 12/2006 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2007027812 | 4/2009 |
| WO | WO-2009055386 A2 | 4/2009 |
| WO | WO2009112786 | 9/2009 |
| WO | WO-2010048021 | 4/2010 |
| WO | WO2010115161 | 10/2010 |
| WO | WO2011011629 | 1/2011 |
| WO | WO2011011741 | 1/2011 |
| WO | WO2011011743 | 1/2011 |
| WO | WO2011038270 | 3/2011 |
| WO | WO2011024077 | 8/2011 |
| WO | WO2011097637 | 8/2011 |
| WO | WO2011127205 | 10/2011 |
| WO | WO2012048226 | 4/2012 |

OTHER PUBLICATIONS

Non-Final Office Action; U.S. Appl. No. 12/625,473; dated Jul. 12, 2012; 10 pages.
Non Final Office Action; U.S. Appl. No. 12/753,751; dated Oct. 5, 2012, 8 pages.
Non-Final Office Action; U.S. Appl. No. 13/074,956; dated Oct. 1, 2012, 8pages.
Wahlen CH et al. "The BioEnterics Intragastric Balloon: How to use it" Obesity Surgery 2001; 11:524-527.
European Supplementary Search Report; EP Application No. 10802994.3, Applicant: ReShape Medical, Inc., mailed Jun. 28, 2013, 8 pgs.
European Supplementary Search Report; EP Application No. 10802918.2, Applicant: ReShape Medical, Inc., mailed Jun. 5, 2013, 6 pgs.
European Search Report—Supplementary; EP 03726447.0, Applicant: Applied Medical Resources Corporation: Mar. 1, 2006, 3 pgs.
Final Office Action; U.S. Appl. No. 11/694,536, Mailing Date Mar. 11, 2011, 13 pages.
Final Office Action; U.S. Appl. No. 11/768,152, Mailing Date Jan. 19, 2011, 13 pages.
International Search Report; International Application No. PCT/US2010/042948; Applicant: ReShape Medical, Inc., Mailing Date Apr. 1, 2011, 11 pages.
International Search Report; International Application No. PCT/US2010/043134; Applicant: ReShape Medical, Inc., Mailing Date Apr. 27, 2011, 12 pages.
International Search Report; International Application No. PCT/US2010/043136; Applicant: ReShape Medical, Inc., Mailing Date Apr. 12, 2011, 9 pages.
International Search Report; International Application No. PCT/US2010/050260; Applicant: ReShape Medical, Inc., Mailing Date: Jun. 17, 2011, 9 pages.
International Search Report; International Application No. PCT/US2011/026233; Applicant: ReShape Medical, Inc., Mailing Date Apr. 26, 2011, 9 pages.
International Search Report; International Application No. PCT/US2011/031463; Applicant: ReShape Medical, Inc., Mailing Date: Jun. 27, 2011, 10 pages.
International Search Report; International Application No. PCT/US2003/012782, Applicant: Applied Medical Resources Corporation, dated: Oct. 28, 2003, 7 pages.
International Search Report; International Application No. PCT/US2006/042336, Applicant: Abdominus, Inc., dated: Mar. 14, 2007, 9 pages.
International Search Report; International Application No. PCT/US2006/042710, Applicant: Abdominus, Inc. et al., dated: Mar. 15, 2007, 9 pages.
International Search Report; International Application No. PCT/US2006/042711, Applicant: Abdominus, Inc. et al, dated: Mar. 16, 2007, 9 pages.
International Search Report; International Application No. PCT/US2006/048647, Applicant: Abdominus, Inc. et al., dated: May 22, 2007, 12 pages.
International Search Report; International Application No. PCT/US2008/058677, Applicant: ReShape Medical et al., dated: Aug. 21, 2008, 12 pages.
International Search Report; International Application No. PCT/US2008/068058, Applicant: ReShape Medical, Inc. et al, dated: Nov. 19, 2008, 11 pages.
International Search Report; International Application No. PCT/US2010/029865, Applicant: ReShape Medical, Inc., dated: Jan. 5, 2011, 9 pages.
International Search Report; International Application No. PCT/US2011/024077; Applicant: ReShape Medical, Inc., dated: Apr. 6, 2011, 12 pages.
International Search Report; International Application No. PCT/US2011/024082, Applicant: ReShape Medical, Inc., dated: Apr. 6, 2011, 10 pages.
International Search Report; International Application No. PCT/US1155373, Applicant: Reshape Medical, Inc., dated: Jan. 20, 2012, 7 pages.
"Living with the BIB: BioEnterics Intragastric Balloon Program: Patient Information"; INAMED Health: Bioenteris Corporation, ECO-SBA-10434; dated Apr. 20, 2004 and May 14, 2005, located online at: www.sydneyobesity.com.au/pdf/M946-01.pdf; 10 pages.
Non-Final Office Action; U.S. Appl. No. 11/694,536; dated: Oct. 26, 2011, 13 pages.
Non-Final Office Action; U.S. Appl. No. 12/625,473; dated Oct. 24, 2011, 18 pages.
Non-Final Office Action; U.S. Appl. No. 12/723,545; dated Feb. 29, 2012, 10 pages.
"ReShape Inflatable Gastric Balloon Going on Trial as Weight Loss Option," MedGadget: Internet Journal of Emerging Medical Technologies. Feb. 4, 2010, 5 pages.
Extended European Search Report; Application No. EP11766679.2, Applicant: Reshape Medical, Inc., mailed Dec. 12, 2013, 6 pages.
Extended European Search Report; Application No. EP11748141.6, Applicant: Reshape Medical, Inc., mailed Feb. 25, 2014, 6 pages.
Final Office Action; U.S. Appl. No. 13/858,767, Mailing Date May 22, 2013, 12 pages.
Extended European Search Report; Application EP11740536.5, Applicant: ReShape Medical, Inc., mailed Jul. 3, 2014, 8 pages.
Extended European Search Report; Application EP11831683.5, Applicant: Reshape Medical, Inc., mailed Jul. 3, 2014, 8 pages.
Final Office Action; U.S. Appl. No. 13/556,0-32, mailed on Jan. 28, 2014, 8 pages.
Non-Final Office Action; U.S. Appl. No. 13/386,650: mailed on Jun. 3, 2014, 15 pages.
Notice of Allowance; U.S. Appl. No. 12/753,603, dated May 13, 2014, 18 pages.
Ostrovsky, ReShape Inflatable Gastric Balloon going on Trial as Weight Loss Option; http://www.medgadget.com/2010/02/reshape_inflatable_gastric_balloon_system_going_on_trial_as_$_{L\,wieight}$_loss_option.html Feb. 4, 2010, retrieved on 02-10-2-13.

* cited by examiner

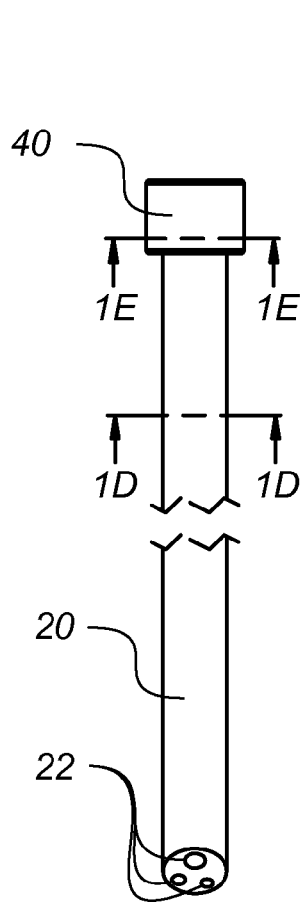
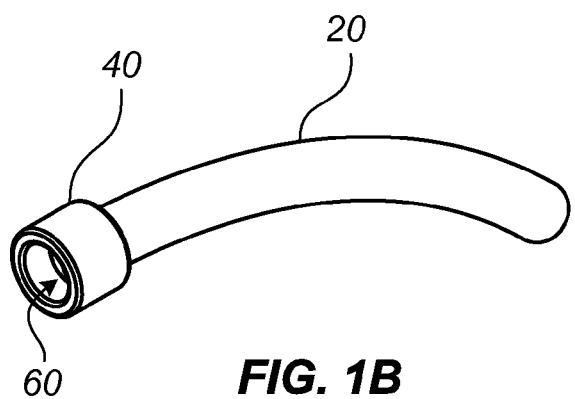
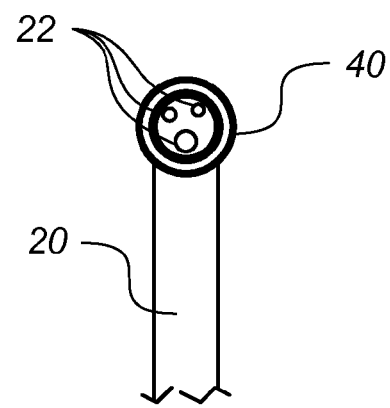
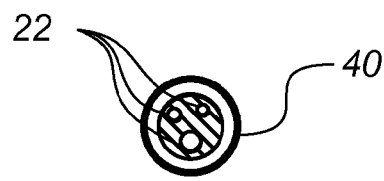
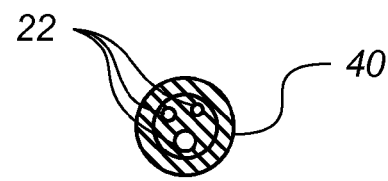
FIG. 1A
FIG. 1B
FIG. 1C
FIG. 1D
FIG. 1E

NORMALIZATION AND STABILIZATION OF BALLOON SURFACES FOR DEFLATION

RELATED APPLICATION

The present application is a U.S. National Phase application under 35 U.S.C. 371 of International Application Serial No. PCT/US2010/050260, filed Sep. 24, 2010, which claims the benefit of U.S. Provisional Patent Application Ser. No. 61/245,630, filed Sep. 24, 2009, and U.S. Provisional Patent Application Ser. No. 61/330,188, filed Apr. 30, 2010, the entire contents of which are incorporated herein by reference in their entireties.

BACKGROUND

Field

This disclosure relates to devices and methods for operating on an implantable and inflatable balloon device. More particularly, this disclosure relates to a device and method for providing a proper configuration and orientation for puncturing and aspirating an implantable and inflatable balloon device.

SUMMARY

Briefly stated, a deflation device is disclosed according to embodiments, comprising, in combination: an endoscope tube, having a distal end, a proximal end, and a lumen; a cap disposed at the distal end of the endoscope tube and having walls defining a balloon interface chamber; a coring device disposed within the lumen and configured to travel within the lumen such that a distal end of the coring device is extendable beyond the distal end of the cap; and wherein the cap is configured to cause a portion of a surface of a balloon to be orthogonal to a longitudinal axis of the coring device as the coring device is disposed near the distal end of the cap.

The cap may further comprise a flexible distal portion and a rigid proximal portion. The cap may further comprise a protrusion extending radially inward from the walls of the cap, the walls defining a coring channel. The protrusion may be configured to guide the coring device to an orientation perpendicular to the balloon. The protrusion may be an annular ring. The protrusion may be tapered and the coring channel may be a frustoconical space having a proximal aperture smaller than a distal aperture. The protrusion may define a guiding channel for the coring device, wherein the guiding channel may be of a diameter substantially equal to the diameter of the coring device.

The deflation device may further comprise a vacuum device in fluid communication with the balloon interface chamber. The vacuum device may be in fluid communication with the balloon interface chamber via the lumen.

According to embodiments, disclosed is a method for deflating an inflated balloon device, comprising, in combination: advancing a deflation device to a balloon until a cap at a distal end of the deflation device contacts a surface of the balloon, the cap and the surface of the balloon defining a balloon interface chamber; applying a vacuum to the balloon interface chamber, whereby a portion of the surface enclosing the balloon interface chamber is drawn into a convex shape; advancing the coring device from a lumen of the deflation device through a coring channel defined by a protrusion extending radially inward from walls of the cap, whereby a tip of the coring channel is deflected by the protrusion to be made orthogonal to the surface of the balloon at a site of penetration; penetrating the balloon with the coring device at a site of penetration; and aspirating fluid from within the balloon through the site of penetration.

The protrusion may be an annular ring. The protrusion may be tapered and the coring channel may be a frustoconical space having a proximal aperture smaller than a distal aperture. The protrusion may define a guiding channel for the coring device, wherein the guiding channel may be of a diameter substantially equal to the diameter of the coring device. Advancing the coring device within the lumen to the balloon further comprises advancing the coring device against a protrusion extending radially inward from the walls of the cap, whereby the coring device is aligned to be at least substantially orthogonal with a portion of the balloon surface.

According to embodiments, disclosed is a deflation device, comprising, in combination: an endoscope tube, having a distal end, a proximal end, and a lumen; a cap disposed at the distal end of the endoscope tube and having walls defining a balloon interface chamber at a distal end of the cap, the balloon interface chamber being in communication with the lumen; a coring device disposed within the lumen and configured to travel within the lumen such that a distal end of the coring device is extendable beyond the distal end of the cap; a vacuum chamber at the distal end of the cap; and a vacuum line fluidly connected to the vacuum chamber, wherein the vacuum chamber is configured to interface with a surface of a balloon and secure the cap thereto when vacuum pressure is applied.

The vacuum chamber may be an annular ring concentric with the balloon interface chamber. The vacuum chamber may be separated from the balloon interface chamber by a septum.

According to embodiments, disclosed is a method for deflating an inflated balloon device, comprising, in combination: advancing a deflation device to a balloon until a cap of the deflation device contacts a surface of the balloon, whereby a balloon interface chamber and a vacuum chamber of the cap are enclosed partly by the surface of the balloon; providing vacuum to the vacuum chamber, whereby the cap is secured relative to balloon and a portion of the surface enclosing the balloon interface chamber is substantially flat and orthogonal to a longitudinal axis of a coring device within the deflation device; advancing the coring device, whereby the balloon is penetrated at a site of penetration; and aspirating fluid from within the balloon through the site of penetration.

Providing vacuum to the vacuum chamber may be effectuated through a vacuum line in fluid communication with the vacuum chamber. The vacuum chamber may surround the balloon interface chamber. Providing vacuum to the vacuum chamber may cause the portion of the surface enclosing the balloon interface chamber to be stretched flat. Providing vacuum to the vacuum chamber may cause the portion of the surface enclosing the balloon interface chamber to be stretched flat.

DRAWINGS

The above-mentioned features and objects of the present disclosure will become more apparent with reference to the following description taken in conjunction with the accompanying drawings wherein like reference numerals denote like elements and in which:

FIG. 1A shows a view of an endoscope with cap, according to embodiments of the present disclosure;

FIG. 1B shows a perspective view of an endoscope with cap, according to embodiments of the present disclosure;

FIG. 1C shows a front view of an endoscope with cap, according to embodiments of the present disclosure;

FIG. 1D shows a sectional view of an endoscope with cap, according to embodiments of the present disclosure;

FIG. 1E shows a sectional view of an endoscope with cap, according to embodiments of the present disclosure;

FIG. 4A shows a perspective view of a cap, according to embodiments of the present disclosure;

FIG. 4B shows a perspective view of a cap, according to embodiments of the present disclosure;

FIG. 5A shows a perspective view of a cap, according to embodiments of the present disclosure;

FIG. 5B shows a perspective view of a cap, according to embodiments of the present disclosure;

DETAILED DESCRIPTION

Figure 2:
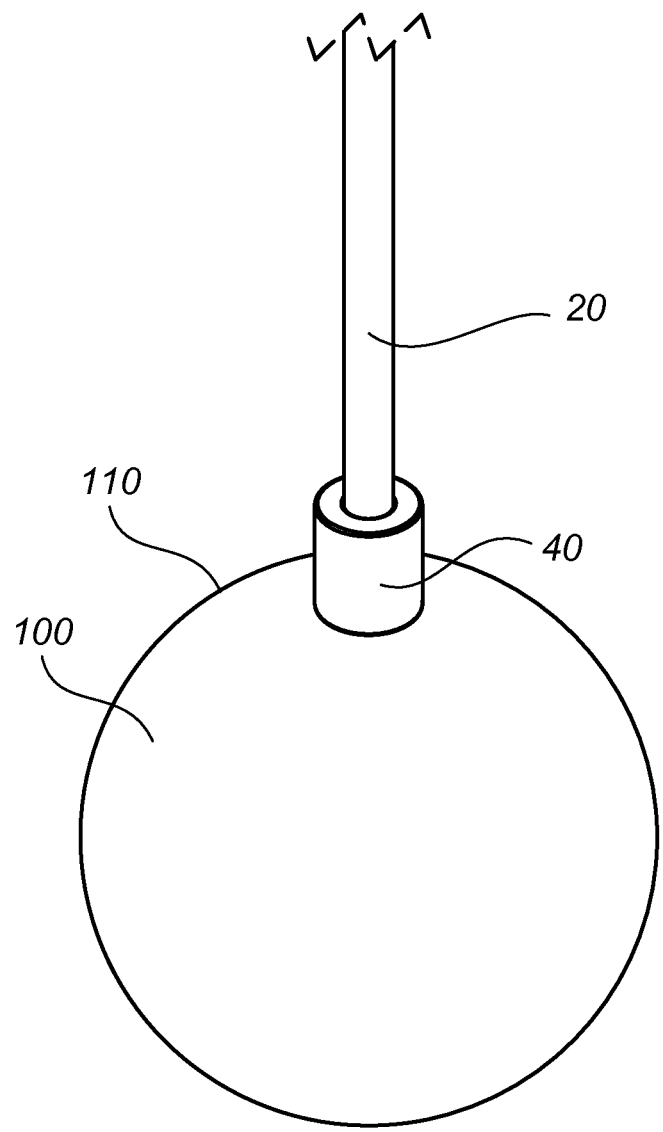
FIG. 2 shows a perspective view of an endoscope with cap engaged on a balloon, according to embodiments of the present disclosure.

Devices for deflation and removal of implantable or inflatable devices are intended to be applied and maintained in a stable and normal fashion to the surface of a balloon wall under stain. By doing so, a full thickness and/or a partial thickness circular cut through the balloon wall is accomplished, reducing the chance for tearing at the coring site, as compared to piercing with a conical, beveled, or facetted needle.

Establishing and maintaining a normal orientation of a coring needle relative to the surface of a balloon to be operated upon may be difficult, as the endoscope catheter used may be flexible and only loosely supported by surrounding anatomy. The balloon may be free to move about and slippery. Both catheter and balloon are subjected to subtle and gross anatomical movement. If the coring needle is not maintained at least substantially orthogonal to the balloon surface, the full thickness and/or a partial thickness cut through the balloon wall may not form the desired complete circle, thereby forming only an incomplete circle. This is not an optimal application of coring for deflation of a balloon under strain, because the terminations or start and ending of the incomplete circle serve as stress risers and can result in small or large tears, corresponding to small or large amounts of undesired fluid leakage from the balloon and an inability to form a seal around the deflation catheter for deflation of the balloon via vacuum.

The inventors of the present disclosure have developed improvements upon devices for deflation of implantable and inflatable devices, such as inflatable intragastric balloons and other medical devices, addressing longstanding needs and avoiding ostensive issues with migration which have plagued clinically relevant devices and methods.

This application incorporates by reference U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; WIPO Pub. No. WO 2007/075810, published May 7, 2007; U.S. patent application Ser. No. 12/723,545, filed on Mar. 12, 2010; PCT App. Ser. No. PCT/US2010/043134, filed on Jul. 23, 2010; each as if fully set forth herein in its entirety.

According to embodiments, the use of endoscopic cap 40 enables the user to normalize a coring needle to balloon surface 110 of balloon 100 and establish a large and stable footprint for puncture at a pre-determined beneficial focal distance, thereby providing the optimal conditions for puncturing the intragastric balloon 100 with a coring needle catheter. The coring needle or other instruments may be delivered to cap 40 via one or more lumens 22 of endoscope 20. Endoscope cap 40 may be attached to the distal tip of endoscope 20, as shown in FIGS. 1A, 1B, 1C, 1D, and 1E. The cap 40 may be permanently (fixedly) attached or temporarily (removably) attached by user. It may be constructed of a rigid or semi-rigid material.

As shown in FIG. 2, by pushing cap 40 onto balloon surface 110, endoscope 20 is indexed at an orthogonal orientation and a large stable contact area, preferably between about 13 mm and about 18 mm in diameter, is created. The device and its dimensions may be scaled to accommodate any purpose. As such, other ranges of dimensions are within the scope of this disclosure. According to embodiments, cap 40 defines and encloses balloon interface chamber 60, connecting the distal end of endoscope 20 with surface 110 of balloon 100.

According to embodiments, contact stability between cap 40 and balloon 100 may be improved by various methods. For example, a user may deflect or retroflex endoscope 20 such that it braces against the nearby gastric wall. By further example, one may provide a high traction engagement surface on cap 40 with a high coefficient of friction material or with surface features such as bumps, indentations, annular rings, or woven fabric to improve contact stability. Further, providing distally extending fingers or projections around the annulus of a distal face of cap 40 may improve contact stability.

According to embodiments, indexing and stability benefits are also achieved by providing endoscopic cap 40 that can apply a vacuum under the whole cap 40 cross-sectional profile or a portion of the profile. As used herein, "vacuum" means a pressure less than at least one of the pressure within balloon 100 and the pressure outside balloon 100, endoscope 20, and cap 40. "Vacuum" refers to providing a pressure that is relatively lower than the pressure of an immediately adjacent space. As used herein, vacuum may not necessarily mean a volume of space that is entirely empty of matter.

According to embodiments, vacuum chamber 50 is provided to interact with surface 110 of balloon 100. As shown in FIGS. 3A, 3B, 3C, 3D, 3E, and 3F, vacuum chamber 50 may be a space defined by an annular ring surrounding balloon interface chamber 60 (i.e., the coring needle site). Such an annular ring provides selectable securement to balloon 100 entirely around balloon interface chamber 60. Other configurations may be provided for vacuum chamber 50. For example, vacuum chamber 50 may be one or more spaces providing various engagement sites. Vacuum chamber 50 may be of any geometry to optimize engagement onto balloon 100.

Figure 3A:
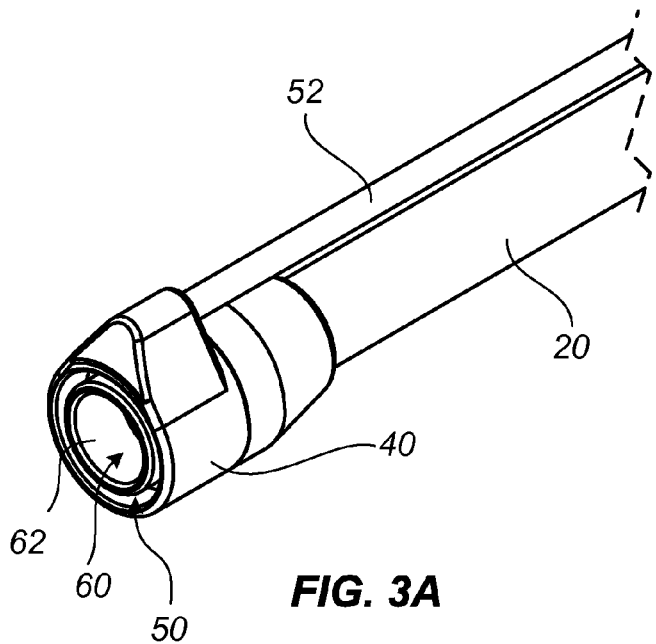
FIG. 3A shows a perspective view of an endoscope with cap having a vacuum chamber, according to embodiments of the present disclosure.
Figure 3B:
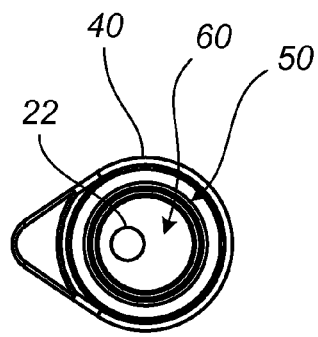
FIG. 3B shows a front view of an endoscope with cap having a vacuum chamber, according to embodiments of the present disclosure.
Figure 3C:
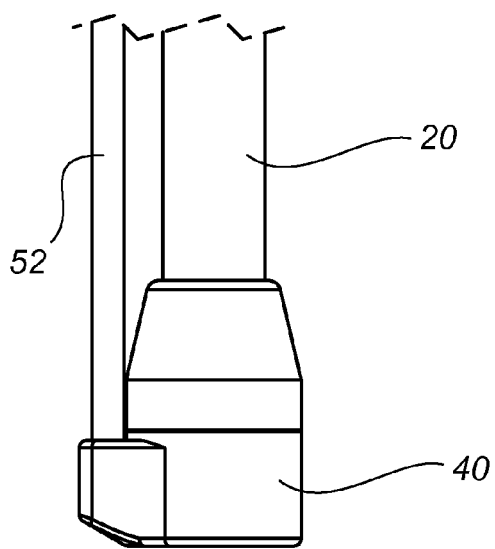
FIG. 3C shows a side view of an endoscope with cap having a vacuum chamber, according to embodiments of the present disclosure.
Figure 3D:
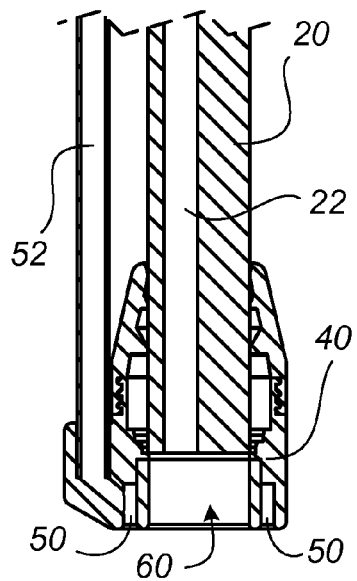
FIG. 3D shows a sectional view of an endoscope with cap having a vacuum chamber, according to embodiments of the present disclosure.
Figure 3E:
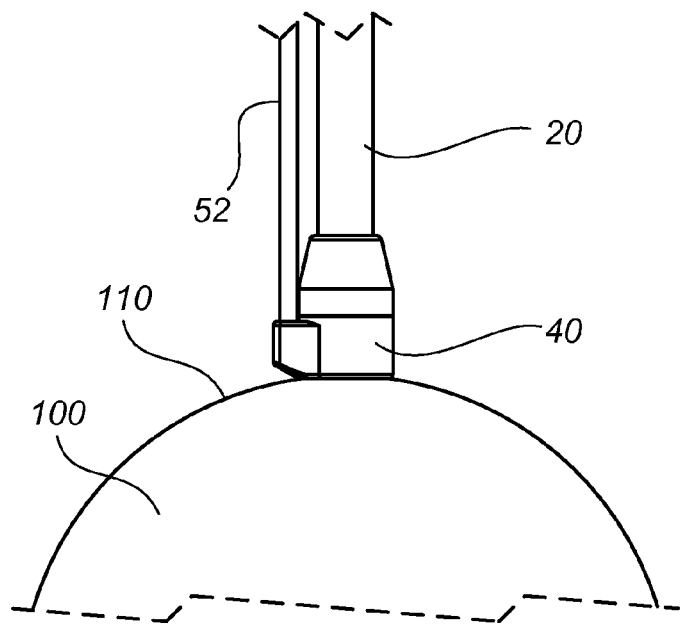
FIG. 3E shows a side view of an endoscope with cap having a vacuum chamber engaged on a balloon, according to embodiments of the present disclosure.
Figure 3F:
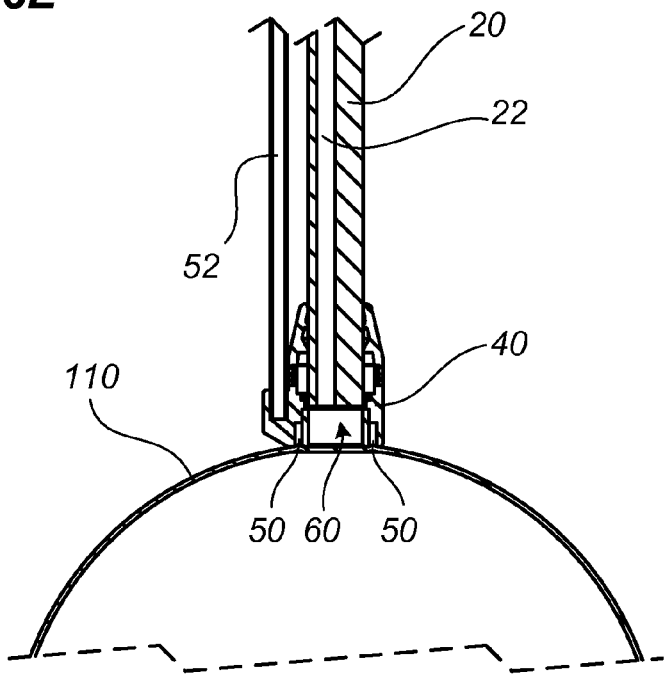
FIG. 3F shows a sectional view of an endoscope with cap having a vacuum chamber engaged on a balloon, according to embodiments of the present disclosure.

There are multiple ways in which vacuum may be achieved for improved stability and to hold onto balloon 100. For example, vacuum line 52 may be provided in communication with vacuum chamber 50 of cap 40. Vacuum may be created under all or a portion of cap 40 footprint through independent vacuum line 52 communicating with the cap 40, as shown in FIG. 3D. Vacuum chamber 50 may be independent of and separate from balloon interface chamber 60.

According to embodiments, vacuum may be created under all or a portion of the cap 40 footprint via communication with vacuum applied through the lumen 22 of the endoscope 20. According to embodiments, vacuum may be created under all or a portion of the cap 40 footprint via communication with vacuum applied through a catheter.

When vacuum is applied to an area surrounding the coring needle site, such as around an annular ring, the vacuum may stabilize and hold the balloon surface 110 without deforming or making surface 110 more convex. This leaves the balloon surface 110 substantially flat (or otherwise conforming to portions of cap 40) and generally orthogonal to lumen 22 of endoscope 20 and does not introduce additional stress or strain to the site of penetration.

According to embodiments, vacuum may be applied to balloon interface chamber 60. For example, vacuum may be applied through one or more lumens 22 or through devices therein.

According to embodiments, balloon interface chamber 60 may be configured to cause surface 110 of balloon 100 to conform to the boundaries thereof. For example, as surface 110 of balloon 100 is drawn into balloon interface chamber 60 due to relatively low pressure therein, portions of surface 110 of balloon 100 may conform to the boundaries of balloon interface chamber 60 such as walls 62 or a distal portion of protrusion 46. This may cause surface 110 of balloon 100 to achieve an orthogonal orientation relative to at least one of coring device 30, lumen 22, and endoscope 20.

According to embodiments, when vacuum is applied to an area including the area to be cored, such as balloon interface chamber 60 or the entire area under cap 40, the surface to be cored may be stabilized by the vacuum hold. At the same time, surface 110 may also deform or be made more convex by the applied vacuum. As a result, balloon surface 110 under cap 40 and aligned with the scope working channel may no longer be orthogonal to lumen 22 (i.e., working channel) of endoscope 20 or coring device 30.

A surface having a tendency to deform at the puncture site for the above reasons or others may still be provided with a normal alignment relative to coring device 30 for puncture. For example, endoscopic cap 40 may have one or more protrusions 46 that deflect tip 32 of coring device 30 as it is extended from lumen 22 of endoscope 20 such that it engages the convex portion of surface 110 of balloon 100 at a normal angle of approach. For example, coring device 30 may naturally extend from lumen 22 of endoscope 20 in a manner that does not naturally provide orthogonal alignment any nearby portion of surface 110. This may be the case where coring device 30 and lumen 22 are not aligned on a central axis of the balloon interface chamber 60.

Figure 4C:
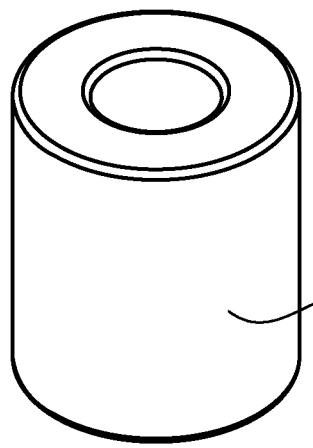
FIG. 4C shows a sectional view of a cap, according to embodiments of the present disclosure.
Figure 4C:
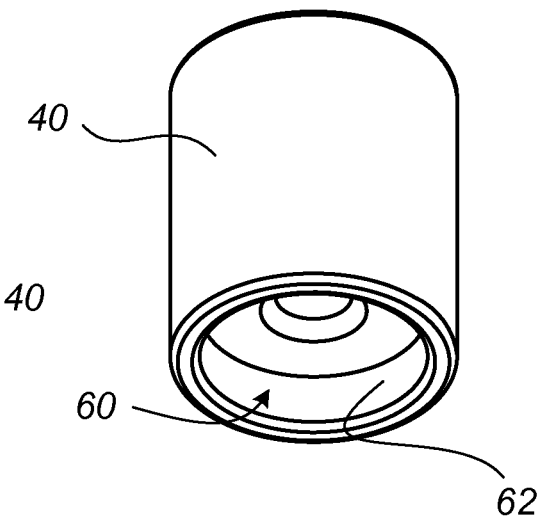
Figure 4C:
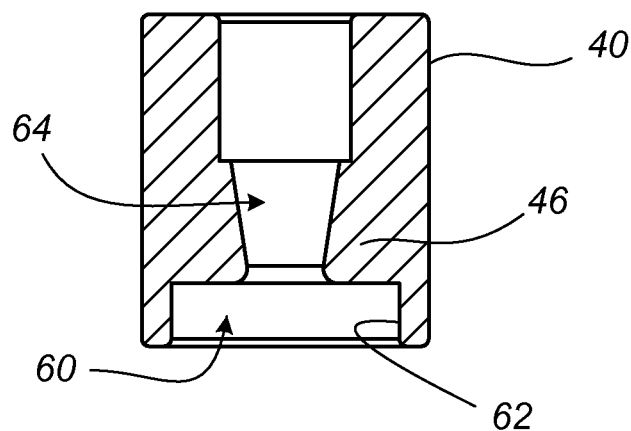
Figure 4D:
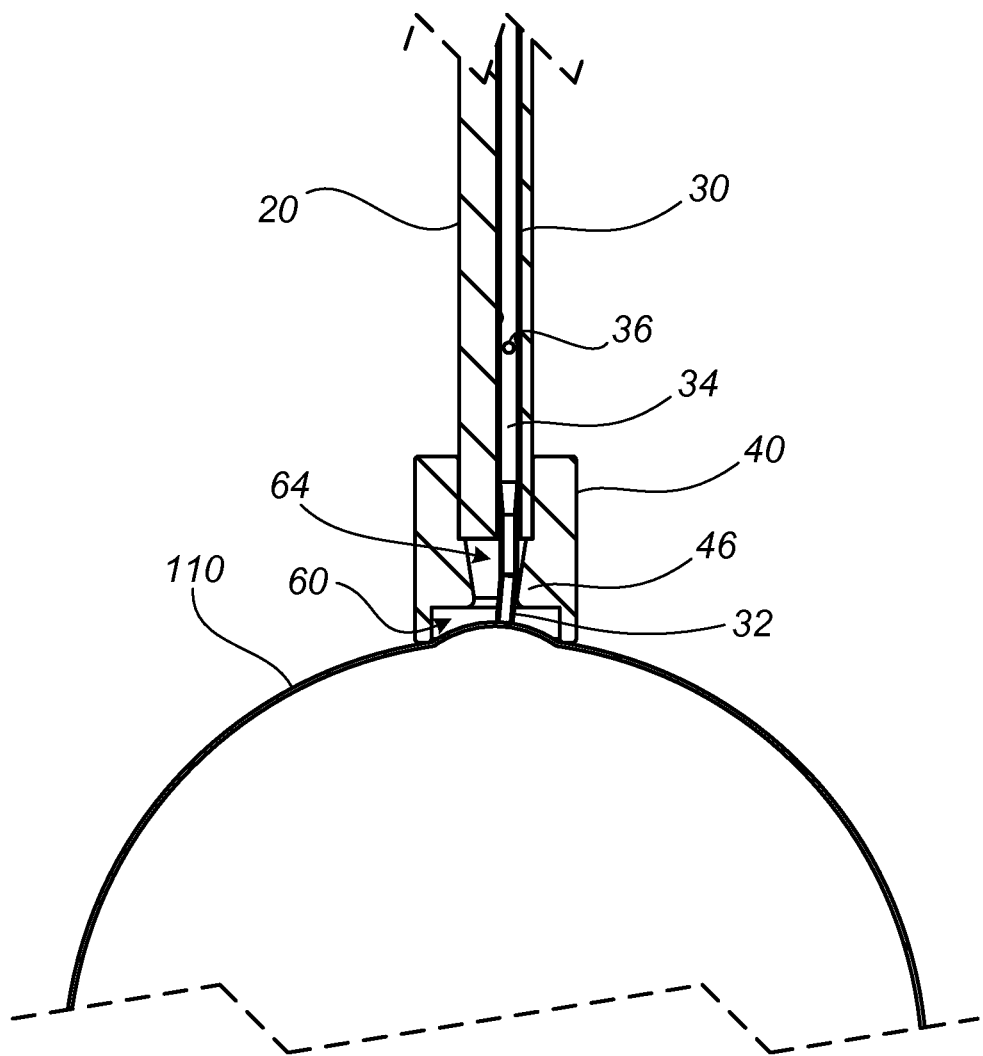
FIG. 4D shows a sectional view of an endoscope with cap engaged on a balloon, according to embodiments of the present disclosure.
Figure 5C:
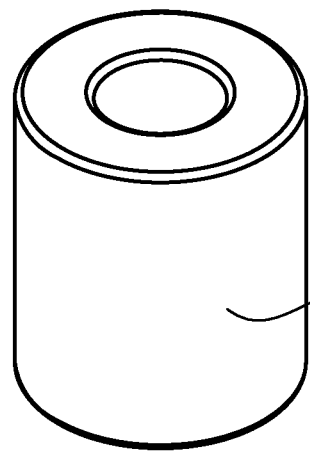
FIG. 5C shows a sectional view of a cap, according to embodiments of the present disclosure.
Figure 5C:
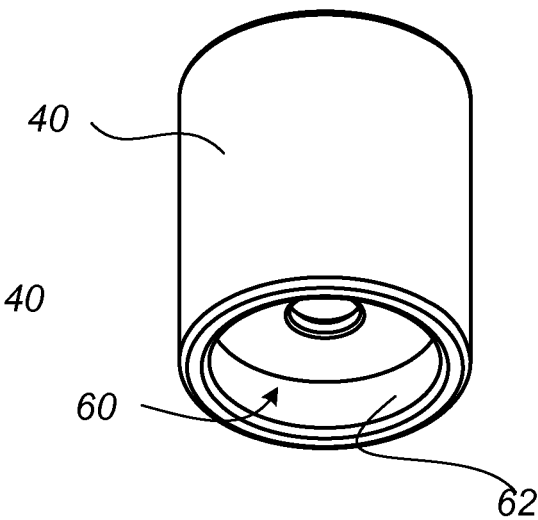
Figure 5C:
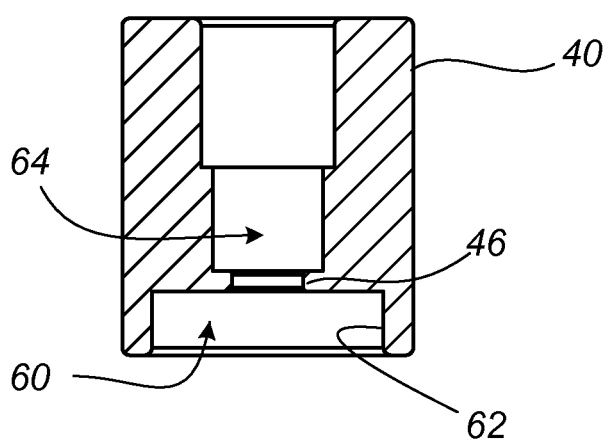
Figure 5D:
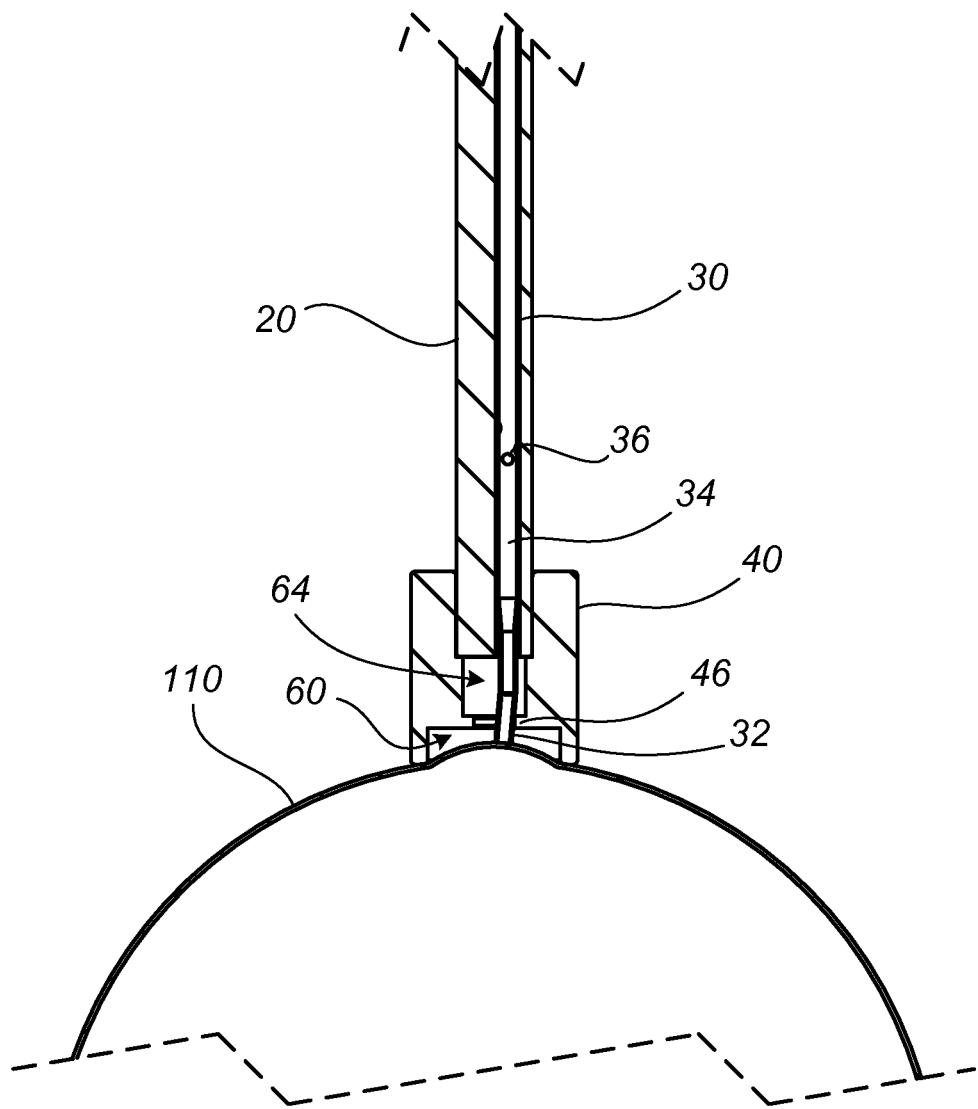
FIG. 5D shows a sectional view of an endoscope with cap engaged on a balloon, according to embodiments of the present disclosure.
Figure 6A:
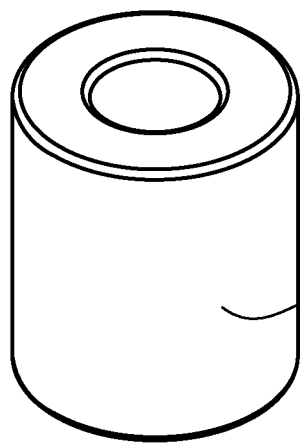
FIG. 6A shows a perspective view of a cap, according to embodiments of the present disclosure.
Figure 6B:
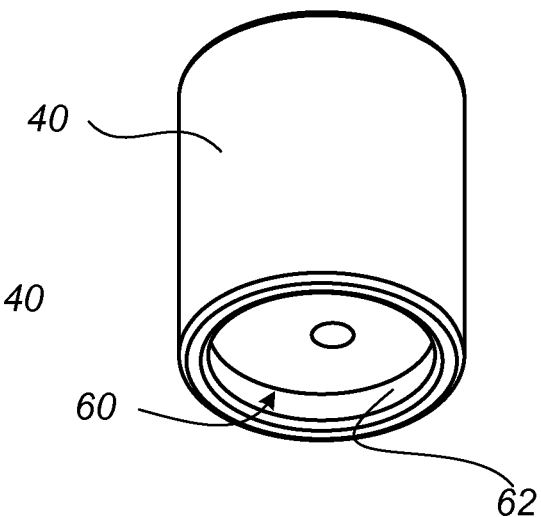
FIG. 6B shows a perspective view of a cap, according to embodiments of the present disclosure.
Figure 6C:
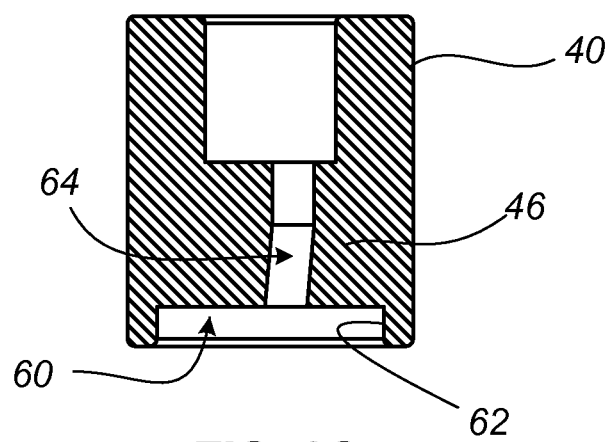
FIG. 6C shows a sectional view of a cap, according to embodiments of the present disclosure.
Figure 6D:
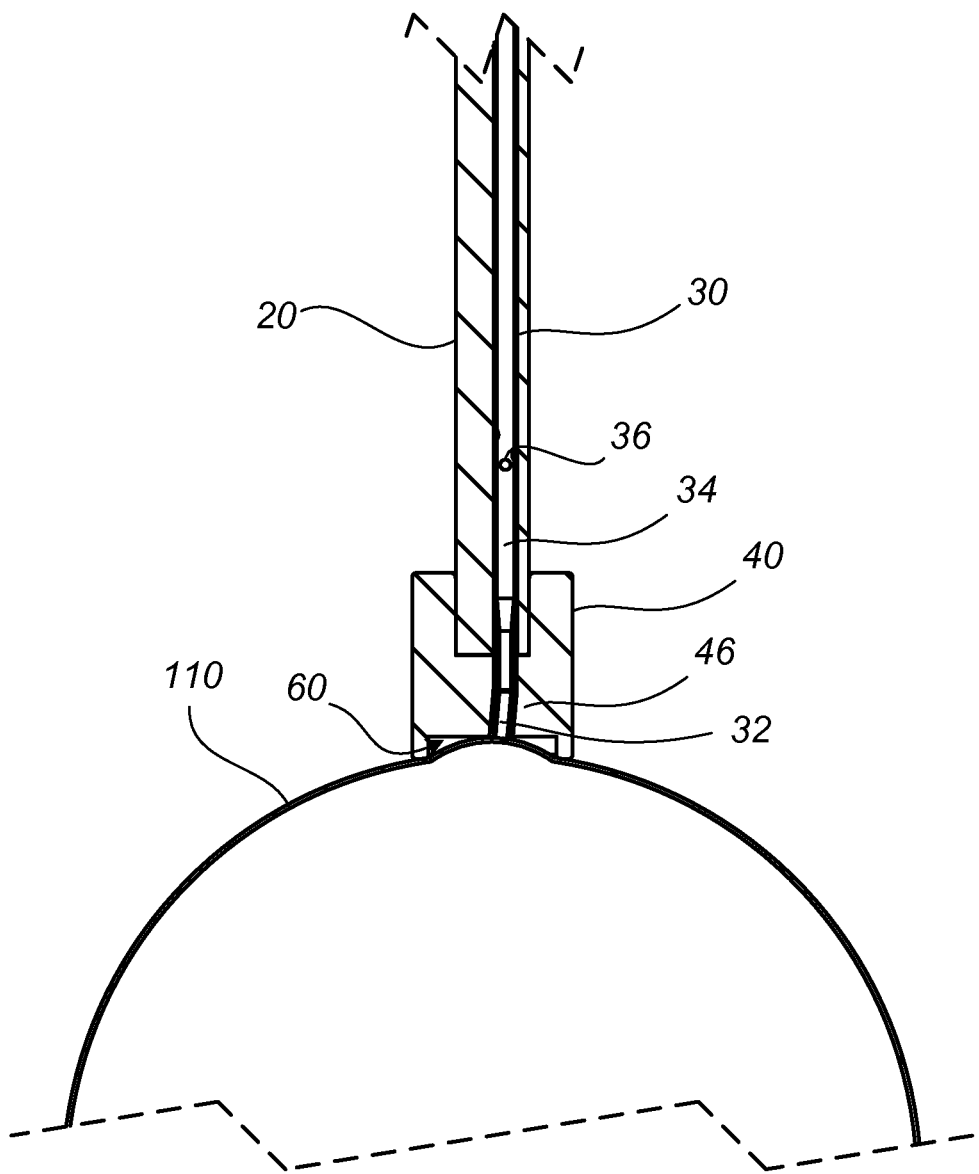
FIG. 6D shows a sectional view of an endoscope with cap engaged on a balloon, according to embodiments of the present disclosure.

According to embodiments, coring channel 64 may be provided to align coring device 30 as it extends from lumen 22. As shown in FIGS. 4D, 5D, and 6D, coring channel 64 spans, is a portion of, or includes the space between the distal end of endoscope 20 and balloon interface chamber 60.

According to embodiments, as shown in FIGS. 4A, 4B, 4C, and 4D, protrusion 46 forms a tapered ring that extends radially inward from walls 62 such that coring device 30 is guided to a preferred orthogonal engagement with the puncture target of surface 110. For example, protrusion 46 may define coring channel 64 as a generally frustoconical space, with a more narrow aperture at its distal end than at its proximal end. The tapered element may provide a gradual transition from lumen 22 to the puncture target while beneficially modifying the angle of incidence of tip 32 relative to surface 110.

According to embodiments, as shown in FIGS. 5A, 5B, 5C, and 5D, protrusion 46 forms a tapered ring that extends radially inward from walls 62 such that coring device 30 is deflected to a preferred orthogonal engagement with the puncture target of surface 110. For example, protrusion 46 may define coring channel 64 as a set of stepped cylindrical spaces, with a more narrow aperture at its distal end than at its proximal end. The more narrow distal aperture provided at protrusion 46 may beneficially modify the angle of incidence of tip 32 relative to surface 110. Tapered ring protrusion 46 may also be viewed as a septum dividing coring channel 64 from balloon interface chamber 60, with a through hole to allow passage of coring device 30.

According to embodiments, as shown in FIGS. 6A, 6B, 6C, and 6D, protrusion 46 forms a tapered ring that extends radially inward from walls 62 such that coring device 30 is deflected to a preferred orthogonal engagement with the puncture target of surface 110. For example, protrusion 46 may define coring channel 64 as a curved, linear, segmented, or other geometric pathway. A broader, more narrow, or equal-sized aperture may be provided at its distal end relative to its proximal end. The more narrow distal aperture provided at protrusion 46 may beneficially modify the angle of incidence of tip 32 relative to surface 110.

According to embodiments, endoscopic cap 40 may have one or more internal features that partially or completely spans the cross-sectional area of cap 40 and engages balloon surface 110 to ensure that the surface is perpendicular to lumen 22 of endoscope 20. Such features may include a rigid or semi-rigid floor or a flexible septum (preferably clear) with a through hole. Alternatively, there may be provided a lumen within cap 40, struts that extend radially inward, or a mesh extending partially or entirely across cap 40.

According to embodiments, indexing and stability benefits may be achieved by providing endoscopic cap 40 with adhesive on an engagement surface of cap 40. The engagement surface may be the most distal portion of cap 40 or any portion that engages surface 110 of balloon 100. The engagement surface may be the entire cross-sectional area of cap 40 or a portion of the cross-sectional area, such as protrusion 46 as an annular ring. For example, cap 40 may be manufactured with adhesive on the engagement surface (e.g. a pressure sensitive adhesive or an adhesive activated by heat, moisture, chemical, etc.). The user may apply an adhesive to the engagement surface before the balloon puncture procedure. The user may deliver the adhesive, such as a liquid adhesive, to the engagement surface during the balloon puncture procedure. The user may activate the adhesive during the balloon puncture procedure by delivering heat, light, energy, liquid, gas, inter alia.

According to embodiments, endoscope 20 with cap 40 according to features of the present disclosure is shown in the figures. A deflation device may include cap 40 of two or more primary components. For example, cap 40 may include a distal portion manufactured from a rigid polymer (such as polycarbonate), and a proximal portion manufactured from a flexible polymer (such as silicone). The soft section allows for various sizes of endoscopes (8.5 mm to 11 mm, for example) to easily fit within cap 40. Endoscope 20 may be fitted by friction, fixed by adhesive, or otherwise attached to cap 40 (e.g., by threading, notches, snaps, etc.). For example, the soft section may provide a friction fit for holding cap 40 to the distal end of endoscope 20 without damaging the scope. The distal section may be clear to not obstruct the view of the target balloon 100. The distal section includes vacuum chamber 50 as depicted in the figures, according to some embodiments. By utilizing an annular vacuum chamber as vacuum chamber 50, balloon 100 is held relative to the scope and stretched substantially flat without deforming balloon 100 into a convex shape in balloon interface chamber 60.

According to embodiments, coring device 30 may facilitate aspiration by providing a channel therein through which fluid at coring tip 32 may be drawn. Accordingly, coring device 30 may be used to penetrate and subsequently aspirate balloon 100 without the need to withdraw coring device 30. According to embodiments, coring device 30 may include one or more aspiration holes 36 that provide fluid communication between an interior channel of coring device 30 with lumen 22 of endoscope 20. According to embodiments, coring device 30 may be withdrawn from within balloon 100 followed by aspiration of fluid through a site of penetration of coring device 30. Engagement of cap 40 onto balloon 100 may be maintained after withdrawal of coring device 30 and during aspiration of balloon 100.

According to embodiments, a balloon deflation procedure is disclosed for execution with use of cap 40 as disclosed herein. The steps disclosed herein may be performed in any variety of sequences adjustable to the circumstances. The steps may be performed partially or in full, or at different times.

According to embodiments, a patient may be provided with an implanted inflatable balloon 100 ready for deflation or removal. Cap 40 may be provided over a distal tip of endoscope 20. At the doctor's discretion, tape, adhesive, or other interface features may be used to secure cap 40 or vacuum line 52 to the body of endoscope 20.

Endoscope 20 may be delivered to the stomach or other cavity with cap 40 attached. At the doctor's discretion, lubricant may be applied to cap 40 to facilitate delivery. With endoscope 20 straight and in the stomach, coring device 30 may be delivered through lumen 22 of endoscope 20. At the doctor's discretion, lubricant may be applied to coring device 30 beforehand. At this point, the advancement of coring device 30 may be limited to the distal end of endoscope 20 or cap 40, limiting interference as balloon 100 is subsequently engaged by cap 40. Endoscope 20 and cap 40 may be delivered to surface 110 of balloon 100 such that balloon surface 110 is generally perpendicular to endoscope 20 or cap 40. Cap 40 may be pressed onto balloon surface 110.

In some embodiments, suction may be applied through vacuum line 52, lumen 22, or another element, as disclosed herein. Vacuum may be provided to balloon interface chamber 60 or vacuum chamber 50. Devices for providing vacuum suction are known in the field and may be located at a proximal end of endoscope 20 to communicate with the distal end through lumen 22, vacuum line 52, or other channels. The user can confirm that cap 40 has a suction hold of balloon surface 110 by verifying on a suction pump gauge that the vacuum is building. Endoscope 20 position may be adjusted as necessary to achieve a suction hold on balloon surface 110. Endoscope 20 may be secured to maintain the scope's position and stability.

Where vacuum suction is provided to balloon interface chamber 60, a portion of surface 110 defining a portion of balloon interface chamber 60 may be made convex, such that it is drawn into cap 40 and toward endoscope 20. Where vacuum suction is provided to vacuum chamber 50, a portion of surface 110 defining a portion of balloon interface chamber 60 may be secured and stretched flat and substantially orthogonal to coring device 30.

With cap 40 suctioned onto balloon surface 110, coring device 30 may be advanced until its catheter tubing tip 32 lightly touches balloon surface 110. The coring device 30 may be rotated, advanced, or operated in some other fashion to achieve penetration of balloon surface 110 and advancement of coring needle 32. Advancement may be performed to the extent desired. Markings may indicate the amount of advancement achieved for comparison with the amount desired. Retraction of coring needle 32 of coring device 30 may then be effectuated.

Fluid from within balloon 100 may be aspirated through lumen 22 of endoscope 20, a lumen of coring device 30, or some other channel, mechanism, or device. Deflation may be effectuated to any desirable degree. Deflation may occur while coring device 30 is extended or after it is retracted. After balloon 100 is partially or completely deflated, suction through the catheter to secure cap 40 to balloon 100 may be discontinued and the device may be removed from balloon 100.

According to embodiments, a patch may be applied to the penetration site using cap 40. A patch such as a woven material, fabric, rubber, polymer, or elastomer may be carried by cap 40 and placed against balloon surface 110. The patch may have adhesive on the surface facing balloon 100. The adhesive may be applied to the patch as explained above. The patch may be attached to balloon surface 110, creating a reinforced puncture target more resistant to tearing or bursting than a non-reinforced balloon 100.

The steps disclosed herein may be repeated for each balloon where multiple-balloon devices are the object of the procedure. After deflating all or a sufficient number of balloons 100, the deflation device may be removed and the balloon device may be retrieved and removed. At the doctor's discretion, cap 40 may be removed prior to ventilating and/or capturing the balloon device.

According to embodiments, a kit of parts is disclosed. One or more kits of parts can be envisioned by the person skilled in the art, the kits of parts to perform at least one of the methods herein disclosed. Likewise, directions for use ("DFU") are included and the device may be part of a surgical tray or other packaged accessory set for surgeries. The kit may be a sub-component of a surgical tray.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A deflation device, comprising, in combination:
   an endoscope tube, having a distal end, a proximal end, and a lumen;
   a cap disposed at the distal end of the endoscope tube and having walls defining a balloon interface chamber;
   a coring device disposed within the lumen and configured to travel within the lumen such that a distal end of the coring device is extendable beyond the distal end of the cap;
   wherein the cap further comprises a protrusion extending radially inward from the walls of the cap, the walls defining a coring channel; and
   wherein the protrusion is configured to guide the coring device to an orientation orthogonal to a surface of a balloon at a site of penetration.

2. The deflation device of claim 1, wherein the cap further comprises a flexible distal portion and a rigid proximal portion.

3. The deflation device of claim 1, wherein the cap is configured to cause a portion of a surface of a balloon to be orthogonal to a longitudinal axis of the coring device as the coring device is disposed near the distal end of the cap.

4. The deflation device of claim 1, wherein the protrusion is an annular ring.

5. The deflation device of claim 1, wherein the protrusion is tapered and the coring channel is a frustoconical space having a proximal aperture smaller than a distal aperture.

6. The deflation device of claim 1, wherein the protrusion defines a guiding channel for the coring device, wherein the guiding channel is of a diameter substantially equal to the diameter of the coring device.

7. The deflation device of claim 1, further comprising a vacuum device in fluid communication with the balloon interface chamber.

8. The deflation device of claim 1, wherein the vacuum device is in fluid communication with the balloon interface chamber via the lumen.

9. A method for deflating an inflated balloon device, comprising, in combination:
   advancing a deflation device to a balloon until a cap at a distal end of the deflation device contacts a surface of the balloon, the cap and the surface of the balloon defining a balloon interface chamber;

applying a vacuum to the balloon interface chamber, whereby a portion of the surface of the balloon enclosing the balloon interface chamber is drawn into a convex shape;

advancing a coring device from a lumen of the deflation device through a coring channel defined by a protrusion extending radially inward from walls of the cap, whereby a tip of the coring channel is deflected by the protrusion to be made orthogonal to the surface of the balloon at a site of penetration;

penetrating the balloon with the coring device at a site of penetration; and aspirating fluid from within the balloon through the site of penetration.

10. The method of claim 9, wherein the protrusion is an annular ring.

11. The method of claim 9, wherein the protrusion is tapered and the coring channel is a frustoconical space having a proximal aperture smaller than a distal aperture.

12. The method of claim 9, wherein the protrusion defines a guiding channel for the coring device, wherein the guiding channel is of a diameter substantially equal to the diameter of the coring device.

13. The method of claim 9, wherein advancing the coring device within the lumen to the balloon further comprises advancing the coring device against a protrusion extending radially inward from the walls of the cap, whereby the coring device is aligned to be at least substantially orthogonal with a portion of the balloon surface.

14. A deflation device, comprising, in combination:

an endoscope tube, having a distal end, a proximal end, and a lumen;

a cap disposed at the distal end of the endoscope tube and having walls defining a balloon interface chamber at a distal end of the cap, the balloon interface chamber being in communication with the lumen;

a coring device disposed within the lumen and configured to travel within the lumen such that a distal end of the coring device is extendable beyond the distal end of the cap;

a vacuum chamber at the distal end of the cap; and a vacuum line fluidly connected to the vacuum chamber, wherein the vacuum chamber is configured to interface with a surface of a balloon and secure the cap thereto when vacuum pressure is applied.

15. The deflation device of claim 14, wherein the vacuum chamber is an annular ring concentric with the balloon interface chamber.

16. The deflation device of claim 14, wherein the vacuum chamber is separated from the balloon interface chamber by a septum.

17. A method for deflating an inflated balloon device, comprising, in combination:

advancing a deflation device to a balloon until a cap of the deflation device contacts a surface of the balloon, whereby a balloon interface chamber and a vacuum chamber of the cap are enclosed partly by the surface of the balloon;

providing vacuum to the vacuum chamber, whereby the cap is secured relative to balloon and a portion of the surface enclosing the balloon interface chamber is substantially flat and orthogonal to a longitudinal axis of a coring device within the deflation device;

advancing the coring device, whereby the balloon is penetrated at a site of penetration; and aspirating fluid from within the balloon through the site of penetration.

18. The method of claim 17, wherein providing vacuum to the vacuum chamber is effectuated through a vacuum line in fluid communication with the vacuum chamber.

19. The method of claim 17, wherein the vacuum chamber surrounds the balloon interface chamber.

20. The method of claim 17, wherein providing vacuum to the vacuum chamber causes the portion of the surface enclosing the balloon interface chamber to be stretched flat.

21. The method of claim 17, wherein providing vacuum to the vacuum chamber causes the portion of the surface enclosing the balloon interface chamber to be stretched flat.

* * * * *